United States Patent [19]
Franck

[11] Patent Number: 6,027,444
[45] Date of Patent: Feb. 22, 2000

[54] VIBRATOR

[75] Inventor: Henrik Franck, Hørsholm, Denmark

[73] Assignee: Multicept APS, Rungsted, Denmark

[21] Appl. No.: 09/267,975

[22] Filed: Mar. 12, 1999

Related U.S. Application Data

[63] Continuation of application No. 08/945,133, Dec. 23, 1997, Pat. No. 5,923,107.

[30] Foreign Application Priority Data

Apr. 21, 1995 [DK] Denmark ................................ 0465/95

[51] Int. Cl.[7] .................................................. A61H 19/00
[52] U.S. Cl. ................................ 600/38; 601/46; 601/72; 310/36; 310/37
[58] Field of Search .......................... 600/41, 38; 607/39, 607/71; 310/36, 37, 38, 80, 47; 601/46, 48, 70, 72

[56] References Cited

U.S. PATENT DOCUMENTS

| | | | |
|---|---|---|---|
| 4,059,100 | 11/1977 | Glage | 128/36 |
| 4,069,816 | 1/1978 | Yamamura et al. | 128/41 |
| 4,079,733 | 3/1978 | Denton et al. | 128/55 |
| 5,067,480 | 11/1991 | Woog et al. | 128/32 |
| 5,195,532 | 3/1993 | Schumacher et al. | 128/739 |
| 5,397,294 | 3/1995 | Hwang | 601/71 |
| 5,519,292 | 5/1996 | Taylor | 318/114 |
| 5,593,381 | 1/1997 | Tannenbaum et al. | 601/93 |

*Primary Examiner*—Nestor Ramirez
*Assistant Examiner*—Burton S. Mullins
*Attorney, Agent, or Firm*—Merchant & Gould PC

[57] ABSTRACT

The invention concerns a vibrator comprising an engagement face (11) which is adapted to engage a part of a body, and which is driven by an electric motor (18). The vibrator moreover comprises a housing (1) comprising a shaft (9) connected with the motor, and the vibrator has a frequency regulating device and an amplitude regulating device (2) for regulating the frequency and the amplitude, respectively, of the upward and downward movement of the engagement face. The vibrator is characterized in that the amplitude regulating device (2) comprises an inclined shaft (15) in extension of the shaft (9) connected with the motor, said inclined shaft being slidably mounted in a conversion element (14) having a through hole. The conversion element (14) is rotatably and slidably mounted in a recess in an arm (13) which is directly secured with respect to the engagement face (11), said recess having a width greater than the width of the conversion element and having an extent in the width which is substantially perpendicular to the direction of the upward and downward movement of the engagement face.

5 Claims, 4 Drawing Sheets

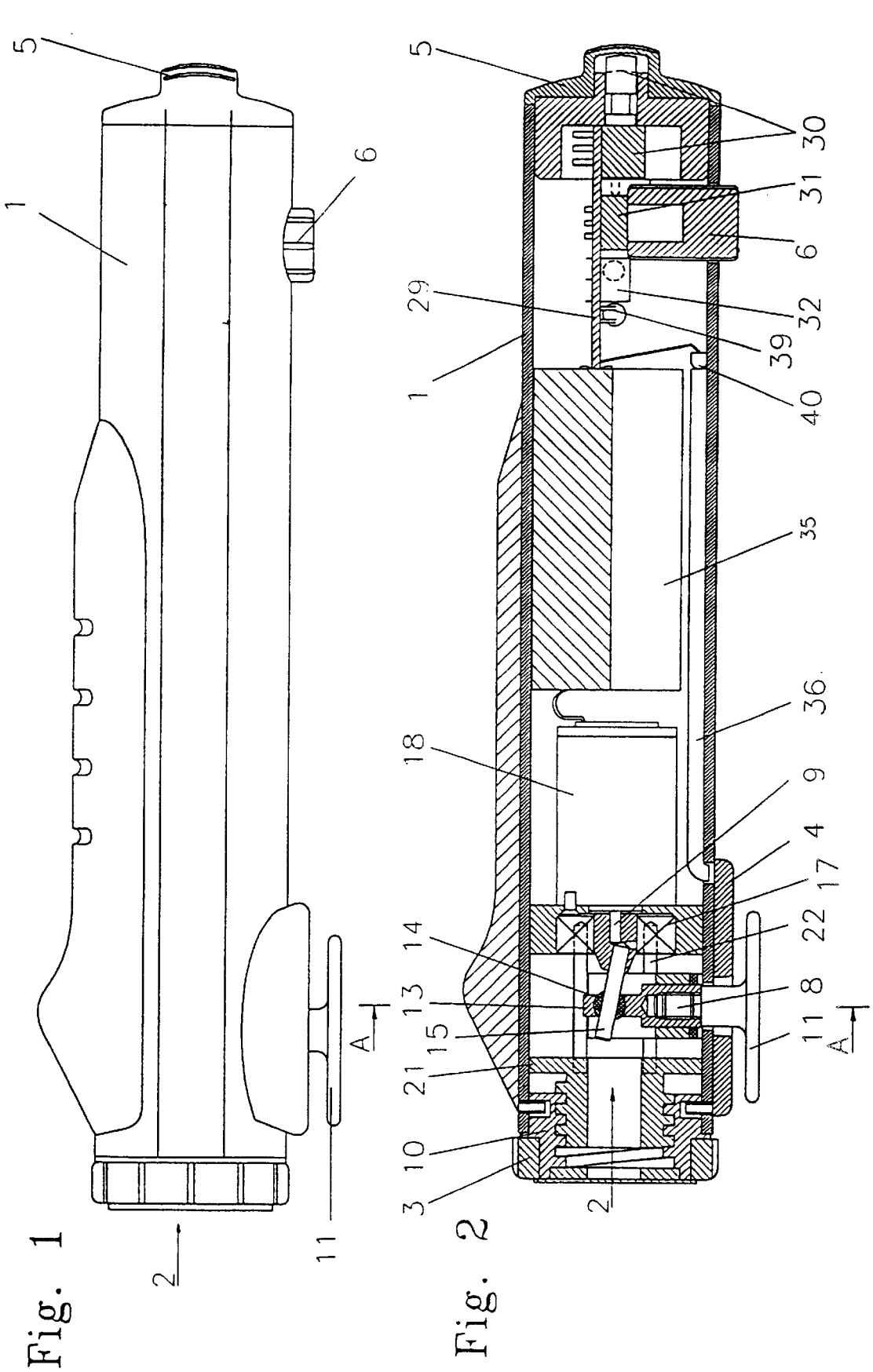

VIBRATOR

This application is a Continuation of application Ser. No. 08/945,133, filed Dec. 23,1997, now U.S. Pat. No. 5,923,107 which applications are incorporated herein by reference.

FIELD OF THE INVENTION

The present invention relates to a method for generating ejaculation in male patients suffering from paralysis by imparting vibrations to the penis.

The invention also relates to a use of a vibrator for the treatment of part of a body and particularly as an aid for generating ejaculation in men.

The present invention concerns a vibrator comprising an engagement face which is adapted to engage a part of a body, and which is driven by an electric motor, and a housing comprising a shaft connected with the motor, and frequency regulating device and an amplitude regulating device for regulating the frequency and the amplitude, respectively, of the upward and downward movement of the engagement face.

It is known that men suffering from paralysis caused by e.g. a spinal injury can ejaculate by imparting vibrations to the penis. However, the required vibration pattern and the necessary period of time for the action on the penis differ from person to person, and moreover depend on the type of injury received by the person concerned.

As an example, reference may be made to "*Clinical Observations in Vibratory Stimulation of the Penis of Men With Spinal Cord Injury*"by George Szasz and Cris Carpenter. In this article a method for generating ejaculation in male patients suffering from spinal cord injuries is described using a Wahl brand, Model 7 in #4820 vibrator. The vibrator is operated at 120 volts and cannot be gripped by one hand while simultaneously gripping around the penis, forcing the engagement face against the penis.

Scientific studies have shown that the ideal vibration is performed at a frequency of 100 Hz and an amplitude of 2.5 mm. At the same time, a force is applied to the penis by the engagement face of the vibrator. The size of this force is difficult to measure, but tests have shown that the necessary counterforce on the other side of the penis is in the range from about 2 to about 15 N.

Therefore, individual adaptation of the vibration pattern to a given group of patients is necessary. Thus, ejaculation may be generated for some patients already at an amplitude of e.g. 1.5 mm, while for others an amplitude of 2.5 mm is necessary. In still others, the amplitude must e.g. be increased after repeated treatments to generate ejaculation.

There is moreover a wish in this group of patients for the ability of vibration treating the penis in private, and accordingly there is an additional need for a vibrator which is easy to carry.

Further, for several reasons, there is a need for a vibrator which can be operated by just one hand. In the first place, one hand operation is desirable, because the other hand may then be used for holding a semen collection container. In addition, many paralyzed men have different hand functions, so that the vibration may be performed with the strongest hand, while the other is perhaps so weak that it cannot be used. Finally, one hand operation is also advantageous with respect to keeping the counterforce on the opposite side of the penis constant, which gives the best result.

Vibrators as an aid for generating ejaculation in men are known. These vibrators are based on a loudspeaker/shaking table principle. This principle requires the use of a large magnet, and the vibrators are therefore constructed as large, heavy table models consisting of several separate units which are connected via wires. These vibrators, which are expensive to manufacture, are difficult to handle and adjust for safe and reliable treatment. Further, they are not suitable for domestic use, since they are stationary and take up relatively much space.

U.S. Pat. No. 827,133 discloses a massage instrument having a device for regulating the amplitude of the engagement face. which takes place by displacing an inclined shaft in a ball having a through hole, said ball being connected with the engagement face via a ball link and a rotary link. The device consists of many parts, which causes the instrument to have a rather high overall height. This is inexpedient, if the instrument is to be used for imparting vibrations to the penis by the use of just one hand.

U.S. Pat. No. 4,088,128 discloses an apparatus for use in connection with beauty treatment of e.g. cheeks and corners of the eye, which apparatus can be held by hand. The apparatus comprises an engagement face and a housing having an electrically driven motor, a self-supplying power unit and a device for regulating the frequency.

U.S. Pat. No. 4,088,128 provides no teachings of means for safe and reliable control of the vibration pattern, and the apparatus cannot therefore be used as an aid for the treatment of other parts of the body, such as the penis, because the required, special vibration pattern of the engagement face cannot be generated. Further, because of its shape the apparatus is inexpedient for the treatment of the penis.

U.S. Pat. No. 3,664,331 discloses a vibrator for the treatment of gums, and also this vibrator has means for regulating the frequency and the amplitude of the engagement face. However, in this apparatus the engagement face performs circular movements, which will not bring about the same effect as the scientifically demonstrated effect of linear upward and downward movements.

The shape of the apparatus is moreover inexpedient for treating the penis, because it is not possible with one hand to provide a counterrest on the opposed side of the penis directly opposite the engagement face.

Accordingly, there is a need for a vibrator which can be handled and be adjusted in a safe manner for safe and reliable treatment, and which is portable and can be employed using just one hand.

SUMMARY OF THE INVENTION

The vibrator of the present invention is characterized in that the amplitude regulating device comprises an inclined shaft in extension of the shaft connected with the motor, said inclined shaft being slidably mounted in a conversion element having a through hole, said conversion element being mounted rotatably and slidably in a recess in an arm which is directly secured with respect to the engagement face, said recess having a width greater than the width of the conversion element and having an extent in the width which is substantially perpendicular to the direction of the upward and downward movement of the engagement face.

As a result, the vibrator may be built as a particularly compact structure having a low overall height which enables it to be used for the treatment of the penis with just one hand.

The structure of the amplitude regulating device ensures that the amplitude of the upward and downward movement of the engagement face may be regulated steplessly and is independent of the applied force. Finally, the amplitude regulating device is formed by just a few mechanical components (inclined shaft, conversion element and arm), which—in addition to the compact structure—also makes the device very reliable.

In use, the engagement face of the vibrator is placed against the part of the body, such as the penis, while the vibrator is held by hand. The treatment of the penis may be effected with one hand, as the compact structure allows the patient to use the thumb of the hand as a counterrest on the opposite side of the penis. Activation of the vibrator causes the engagement face to begin to vibrate, and the rotation of the motor will be converted into an upward and downward movement of the engagement face. By regulating the frequency regulating device and the amplitude regulating device and varying the force applied by the engagement face to the body, the user himself can adapt the vibration for safe treatment.

The method of the present invention is characterized in that the vibration is performed at a frequency in the range of 0 Hz–200 Hz, and that the amplitude is in the range of 1.5 mm–5 mm, and where the engagement face of a vibrator contained in a housing is forced against the penis by the fingers of a hand simultaneously gripping around the penis and the housing of the vibrator, and whereby the frequency and the amplitude of the vibrator is adjusted to satisfy the needs of the individual patient.

In embodiments of the invention, it is ensured that the applied force is carefully controlled, and as the vibrator is manipulated by one hand the patient may use his other hand to collect the semen. Further, this method allows the patient to use the vibrator in private and to adjust the frequency and the amplitude to his needs.

According to claim 2, the conversion element is formed by a ball, and the edges in the recess of the arm have a rounded shape corresponding to the rounded shape of the ball. This results in a structure having simple constructive elements which permit rotation as well as displacement of the conversion element in the recess in a simple manner.

When the ball is ground flat on the sides perpendicular to the through hole, as stated in claim 3, then the ball may be introduced into the recess the "flat way" before the inclined shaft is mounted in the through hole of the bore. It is hereby possible to mount the ball in an arm which is made in one piece, as stated in claim 4.

As stated in claim 5, the amplitude regulation may be performed by means of an adjustment screw which displaces the inclined shaft with respect to the conversion element via threads. The position of the conversion element on the inclined shaft is moved hereby, which results in a change in the amplitude of the engagement face.

In an advantageous embodiment of the invention, the frequency regulating device comprises a device which is adapted to regulate the supply of current and voltage to the electrically driven motor. This provides a simple frequency regulating device which may be made of electronic components, enabling the vibrator to be given a compact structure.

According to claim 7, the apparatus comprises an indicator adapted to apply a signal when the engagement face is subjected to a force which is greater than a given value. This ensures that the user is informed of the size of the force which is applied to the penis. This may be an advantage e.g. to spinally injured men having no sense of touch, because they will be able to regulate the force applied to the engagement face on the basis of the emitted signal, thereby avoiding injury to the tissue because of a too strong force.

According to claim 8, the predetermined value, at which a signal is applied, corresponds to a load of between about 2 and 7 N. This ensures that the indicator applies a signal when the engagement force is subjected to a force which is inexpediently great seen in relation to the ideal vibration pattern. This is an advantage in particular for persons having no sense of touch in the body part which is affected. When the signal is applied by a light diode, a simple indicator is obtained, capable of steplessly informing the user of the force to which the engagement face is subjected. The size of the signal, i.e. the amount of light, may thus vary as ii function of the force. A light diode is a good and effective signal generator for the user, and it has a small power consumption and is easy to incorporate in an electronic unit.

As stated in claim 9, the electrically driven motor may advantageously be built into the housing, and when, as stated in claim 10, the housing is also provided with a self-supplying power unit in the form of an NiCd battery packet, a very compact, easily portable structure is obtained. An NiCd battery packet is an efficient power source which just takes up little space. The battery packet may moreover be charged, so that the user does not have to disassemble the vibrator when the battery packet is no longer capable of supplying a sufficient amount of power. It is moreover ensured that the user is not subjected to dangerous electric shocks, and that the vibrator may be used in all desired surroundings where there is no access to the mains supply.

In use, the engagement face of the vibrator is placed against part of the body, such as the penis, while the vibrator is held by hand. Activation of the vibrator causes the engagement face to begin to vibrate, and the rotation of the motor will be converted into an upward and downward movement of the engagement face. By regulating the frequency and amplitude regulating devices and varying the force applied by the engagement face to the body, the user himself can adapt the vibration for safe treatment.

The invention also relates to a use of a vibrator comprising an engagement face (11) which is adapted to engage a part of a body and a housing (1) which comprises an electrically driven motor (18), a self-supplying power unit and a frequency regulating device adapted to regulate the frequency of an upward and downward movement of the engagement face for treating the penis.

According to claim 2, the vibration is performed at a frequency around 100 Hz and with an amplitude of around 2.5 mm, as these values have been shown to give satisfactory results for most patients.

According to claims 3 and 4 the amplitude and frequencies are adjusted by means of knobs having scales. As the patients do not feel the vibration, it is important that they may know the actual vibration pattern by inspection of the vibrator.

BRIEF DESCRIPTION OF THE DRAWINGS

The invention will be explained more fully below with reference to the drawing, in which FIG. 1 is a perspective view of the vibrator, FIG. 2 is a sectional lateral view of the vibrator.

DETAILED DESCRIPTION OF THE PREFERRED EMBODIMENT

FIG. 1 shows an advantageous embodiment of the vibrator of the invention. The vibrator, which is adapted to generate ejaculation in men, comprises a housing 1 and an engagement face 11. The engagement face 11 is adapted to engage the penis externally. The housing 1 constitutes a storage unit for the technical components of the vibrator as well as a handle for the vibrator.

Figure 3:
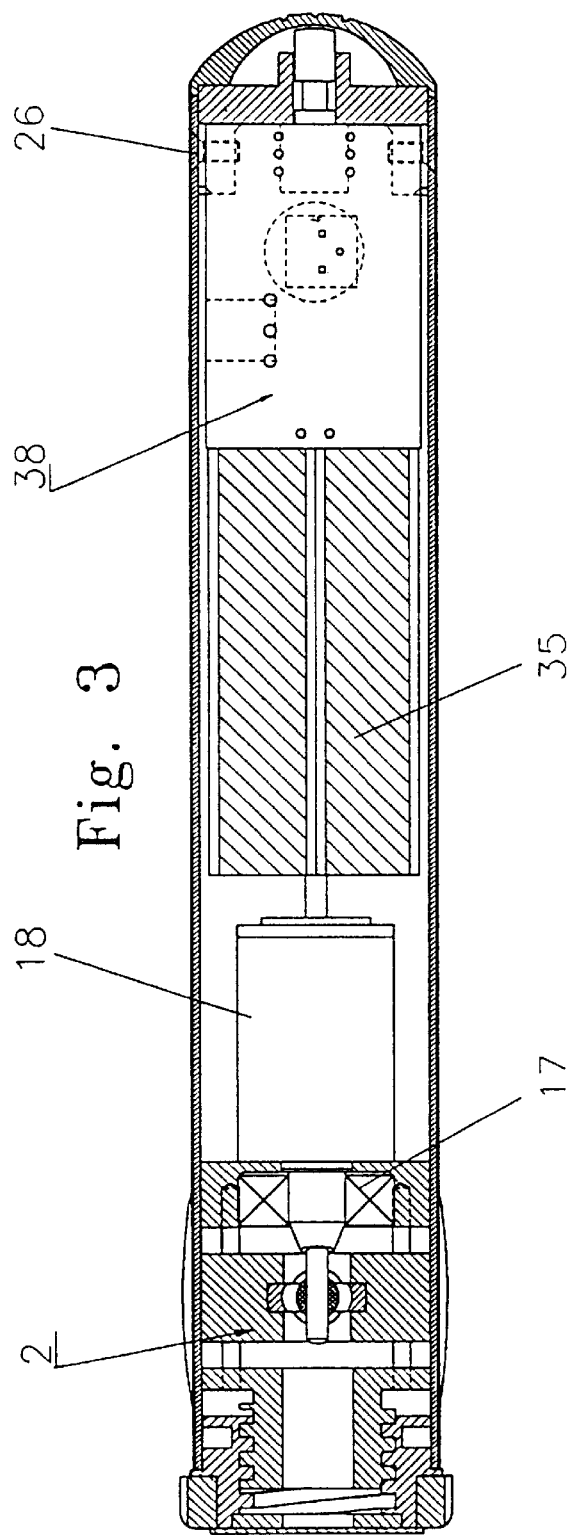
FIG. 3 is sectional top view of the vibrator.

The housing 1, see FIGS. 2 and 3, interiorly accommodates an electrically driven motor 18, which, via the motor shaft 9, drives a shaft 15 inclined with respect thereto. The motor shaft 9 is mounted in a supporting ball bearing 17.

The motor 18 is connected via wires (not shown) to an electronic unit 38 which is supplied with power by the self-supplying power unit. The electronic unit 38 is mounted on a printed circuit board 29.

In the shown embodiment, the self-supplying power unit is formed by a battery packet 35 which consists of chargeable NiCd batteries arranged side by side and in extension of each other. The use of batteries allows the vibrator to be used in all desired surroundings, including locations where there is no access to the mains supply. It is moreover ensured that the user cannot be subjected to dangerous electric shocks if the vibrator is used in moist surroundings, such as e.g. a steamy or wet bathroom.

The batteries may be charged without being removed from the vibrator, through a charger socket 32 which is provided in the side of the vibrator. A light diode 39 signals the charged state of the batteries.

The frequency regulating device is adapted to control the frequency of the vibration. This is done by regulating the voltage supply to the electrically driven motor 18, whereby the frequency, i.e. the number of the upward and downward movements of the engagement face 11 per unit of time, is regulated independently of the load. The frequency is typically regulated in the range from 0 to 200 Hz.

The frequency regulating device is operated via a rubber knob 6 surrounding a potentiometer 31 which is connected to the electronic unit 38.

The housing 1 moreover comprises a mechanical amplitude regulating device 2 which is adapted to regulate the amplitude of the engagement face 11, i.e. the height of the upward and downward movement. The amplitude is typically regulated in the range from 0 to 5 mm, it being recommended to use as small an amplitude as necessary to generate ejaculation. The reason is that the risk of tissue injuries increases when the amplitude is increased.

Figure 4:
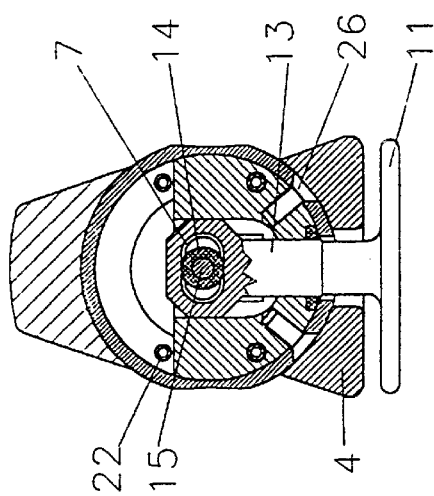
FIG. 4 is an end view of the vibrator along the section A—A.
Figure 5:
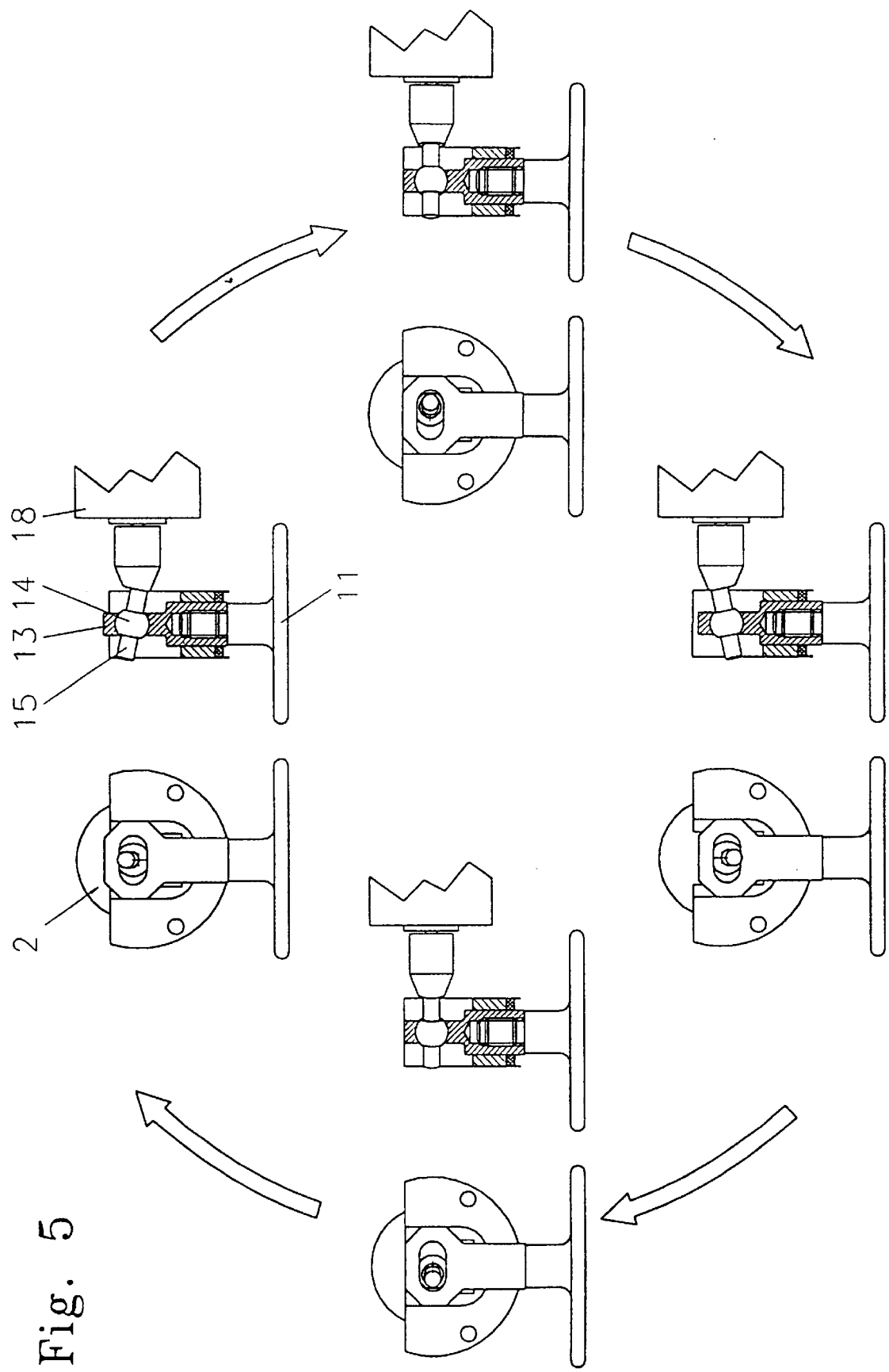
FIG. 5 is a partially sectional view of the amplitude regulating device in four positions during rotation of the motor.

The amplitude regulating device 2 comprises an arm 13 which is formed with a horizontal recess 7, see FIG. 4. This recess 7 accommodates a ball 14 having a through bore. The bore of the ball 14 surrounds a portion of the inclined shaft 15, as is shown in FIG. 3. Thus, rotation of the motor shaft 9 and thereby also of the inclined shaft 15 causes the arm 13 to perform an upward and downward movement. This mechanism is shown in greater detail in FIG. 5, in which the amplitude regulating device 2 is shown in four different positions through a cycle of rotation. FIG. 5 shows each position partly from the end of the amplitude regulating device 2 and partly in a section through the arm 13. As the arm 13 is secured at its lower end with respect to the engagement face 11, said face will likewise perform an upward and downward movement.

The motor 18 is connected with a threaded guide 21 via four shafts 22 and is thus movable to and fro inside the housing 1. This is done by rotating an amplitude regulating knob 10 via a rubber part 3, which is arranged at the end of the housing 1, as this converts rotary movement to a linear sliding movement of the motor 18 via the threaded guide 21. The inclined shaft 15 will hereby also be moved to and fro in the ball 14. Depending on the position of the inclined shaft 15 with respect to the arm 13, the amplitude of the engagement face 11 may thus be regulated. Thus, the amplitude increases when the motor 18 is moved in a direction away from the arm 13, and correspondingly decreases when the motor 18 is moved in a direction toward the arm 13. The reason is that the shaft 15 is inclined.

The ball 14 has a smaller diameter in the direction of the bore, which appears clearly from FIG. 5. The ball may hereby easily be mounted in the recess 7 of the arm, and the ball 14 cannot drop out when the inclined shaft 15 is positioned in the bore. This provides a very simple amplitude regulating device allowing the amplitude to be regulated steplessly and to be independent of the force applied to the engagement face. Finally, the amplitude regulating device only has few mechanical components (inclined shaft, ball and arm).

The amplitude regulating knob 10 is provided thereon with a rubber part having a scale 3 for the reading of the amplitude of the vibrator.

The vibrator, which is shown in FIGS. 1–4, moreover comprises a light diode 40 and a fluorescent tube 36 which signal the user when the engagement face 11 is subjected to a force which is inexpediently great seen in relation to the ideal vibration pattern, and which also emit an increasing amount of light when the force increases. Thus, the signal is variable, and in another embodiment of the invention the light diode 40 might e.g. have three different colours, each of which emits light at a different load.

This reduces the risk of tissue injuries, one reason being that a paralyzed person who cannot feel the force on the penis is informed via the indicator that the load is inexpediently great. The inexpedient force is in the range which corresponds to a counterforce on the opposed side of the penis of about 5 to 7 N and more, but differs from person to person. The force applied is registered by the electronic unit 38, as the voltage data associated with the force are known.

The predetermined maximum value of the force corresponds to a counterforce on the other side of the penis of between about 2 and 7 N. The light diode 40 thus signals when the vibration pattern is inexpedient.

The necessary supply of current and voltage to the motor 18 increases in step with the load to maintain a predetermined frequency. If the load is increased beyond a predetermined maximum value, the necessary supply of current and voltage no longer keeps step, and the frequency of the engagement face 11 will therefore decrease. If the load is increased additionally, the vibration stops completely.

In the embodiment shown, the fluorescent tube 36 directs light from the light diode 40 to an area externally on the housing 1 which is located at the engagement face 11. At this area the housing 1 is surrounded by a transparent material 4 which causes the area around The engagement face 11 to be illuminated when the indicator is activated, i.e. when the engagement face is subjected to a force which is greater than the predetermined value.

The activation of the light diode 40 takes place in that the electronic unit 38 registers the power consumption of the motor 18.

In the embodiment shown, the vibrator moreover comprises an on/off switch 30 which is provided at the opposite end of the amplitude regulating knob 10 of the vibrator. The on/off switch 30 is activated merely by pressing the end member 5 of the vibrator. The vibrator may thus be operated with just one hand, e.g. by pressing the on/off switch 30 down against a firm base.

The engagement face 11 is moreover secured to the arm 13 via threads 8 and may therefore easily be replaced by e.g. other types of engagement faces.

Figure 6:
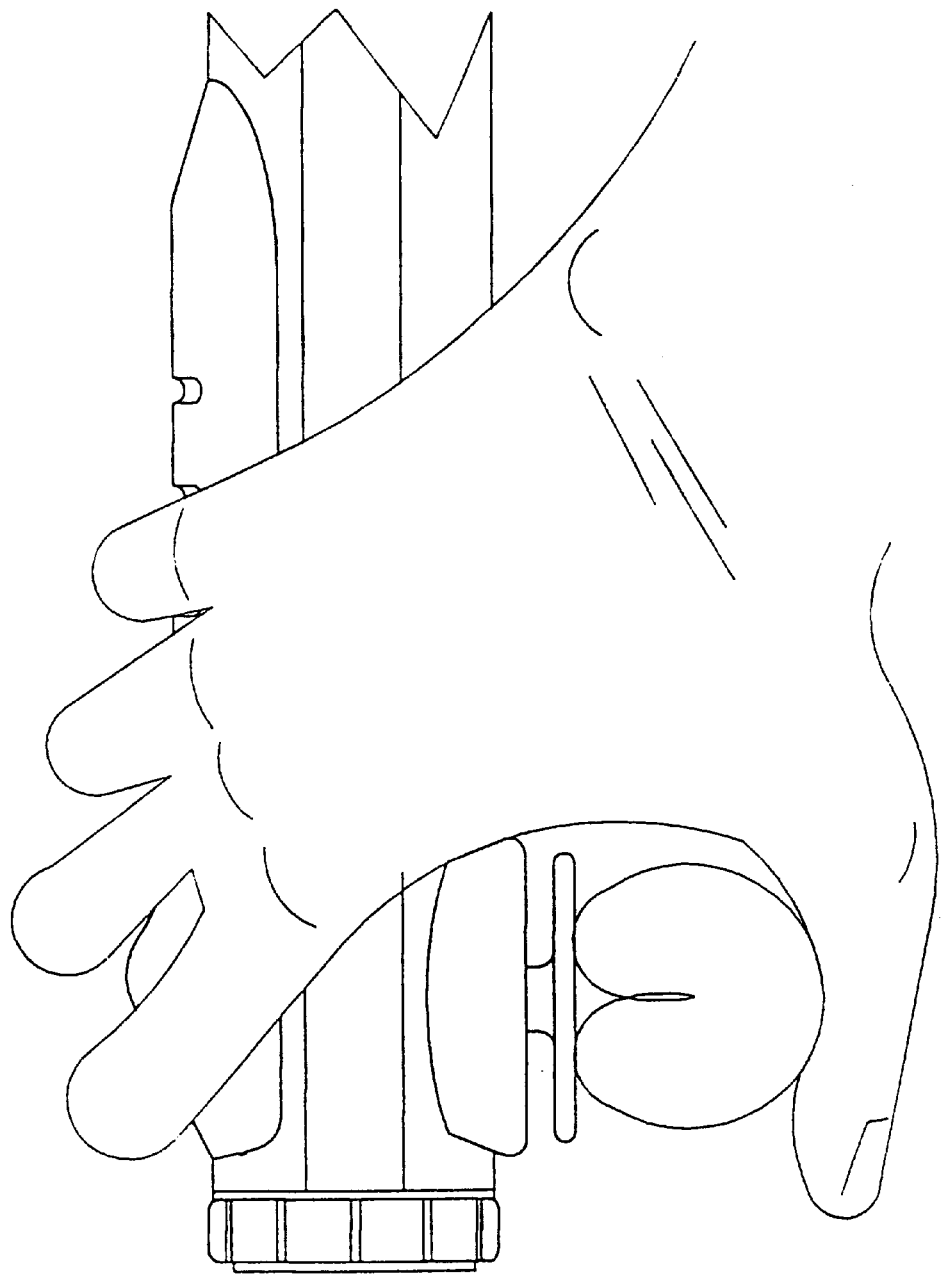
FIG. 6 shows the vibrator used with one hand.

It is shown in FIG. 6 how the vibrator may be used for treating the penis by means of one hand. It will thus be seen that the low overall height of the vibrator, which is a consequence of the compact structure of the amplitude regulating device 2 of the invention, ensures that both the vibrator 1 and the penis 41 may be held between the thumb and the other fingers of the hand. It is hereby relatively easy to maintain a constant counterforce on the penis, which gives the best result in use. Further, the other hand is free e.g. for holding a collection container for the semen.

The individual parts of the vibrator are assembled by means of screws 26 in the embodiment shown, but might also be assembled via snap couplings or the like.

In another embodiment of the invention, the inclined shaft is formed by a bent shaft. This provides the same effect, but obviates the assembly between the motor shaft 9 and the inclined shaft 15.

Many modifications are possible without departing from the idea of the invention. In the embodiment shown, the indicator is e.g. adapted to apply a visual indication, but this indication might also be provided by e.g. a sound signal.

Further, both the frequency regulating device and the amplitude regulating device 2 may be constructed in many ways, e.g. the frequency regulation might take place mechanically, and the amplitude regulation might e.g. take place by displacing the arm 13 instead of the motor 18.

In still another embodiment, the apparatus may have a spring arranged between the housing 1 and the arm 13. Then, depending on the dimensions of the spring, the natural frequency of the system might be regulated so that it e.g. corresponds to the treatment frequency, thereby permitting the battery consumption to be reduced.

The frequency and amplitude regulating devices may likewise be regulated automatically so that one or both of these parameters may vary in time according to a determined pattern.

The apparatus might also be provided with a counterrest which, like the engagement face of the vibrator, engages the penis, merely an its opposed side. The force applied by the engagement face to the penis might hereby be controlled by regulating the force applied by the counterrest.

Finally, the power supply might be separate from the vibrator and merely be connected to it via a wire, and optionally the motor may also be located outside the housing and be connected via a flexible shaft. The hand-operated part of the vibrator will have a considerably reduced weight in such embodiments, which may be an advantage for certain groups of patients.

The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A method for generating ejaculation in male patients suffering from paralysis by imparting vibrations to the penis, wherein the vibration is performed at a frequency in the range of 0 Hz–200 Hz, and that the amplitude is in the range of 1.5 mm–5 mm, and where the engagement face of a vibrator contained in a housing is forced against the penis by the fingers of a hand simultaneously gripping around the penis and the housing of the vibrator, and wherein the frequency and the amplitude of the vibrator is adjusted to satisfy the needs of the individual patient.

2. A method according to claim 1, wherein the vibration is performed at a frequency around 100 Hz, and that the amplitude is around 2.5 mm.

3. A method according to claim 1, wherein the amplitude is adjusted by means of an amplitude regulating knob having a scale for the reading of the amplitude of the vibrator.

4. A method according to claim 1, wherein the frequency is adjusted by means of a frequency regulating knob.

5. The use of a vibrator, comprising:

an engagement face which is adapted to engage a part of a body;

and a housing which comprises,
an electrically driven motor (18);
a self-supplying power unit; and
a frequency regulating device adapted to regulate the frequency of an upward and downward movement of the engagement face, for treating the penis;

wherein the vibration applied to the penis is performed at a frequency in the range of 0 Hz–200 Hz and where the engagement face of the vibrator contained in the housing is forced against the penis by the fingers of a hand simultaneously gripping around the penis and the housing of the vibrator.

* * * * *